(12) United States Patent
Bernhardt et al.

(10) Patent No.: US 7,260,169 B2
(45) Date of Patent: Aug. 21, 2007

(54) DEVICE AND METHOD FOR COMPUTER TOMOGRAPHY

(75) Inventors: Philipp Bernhardt, Forchheim (DE); Jan Boese, Eckental (DE); Ernst Peter Rührnschopf, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/455,245

(22) Filed: Jun. 16, 2006

(65) Prior Publication Data

US 2006/0285630 A1 Dec. 21, 2006

(30) Foreign Application Priority Data

Jun. 17, 2005 (DE) .................... 10 2005 028 216

(51) Int. Cl.
*G21K 1/12* (2006.01)
(52) U.S. Cl. .............................. 378/4; 378/19
(58) Field of Classification Search .................. 378/4, 378/5, 19, 21–25, 108–114, 901
See application file for complete search history.

(56) References Cited

U.S. PATENT DOCUMENTS

| 3,895,313 | A | 7/1975 | Seitz |
| 5,078,551 | A | 1/1992 | Oomen |
| 5,245,189 | A | 9/1993 | Satoh |
| 5,252,840 | A | 10/1993 | Shiomi |
| 5,278,431 | A | 1/1994 | Das |
| 5,399,247 | A | 3/1995 | Carey |
| 5,404,835 | A | 4/1995 | Yoder |
| 5,541,423 | A | 7/1996 | Hirabayashi |
| 6,222,907 | B1 | 4/2001 | Gordon, III et al. |
| 2006/0002509 | A1* | 1/2006 | Claus et al. ............... 378/21 |
| 2006/0067461 | A1* | 3/2006 | Yin et al. .................. 378/5 |
| 2006/0109949 | A1* | 5/2006 | Tkaczyk et al. ........... 378/4 |
| 2006/0159223 | A1* | 7/2006 | Wu et al. ................. 378/18 |

FOREIGN PATENT DOCUMENTS

DE 100 51 462 A1 4/2002

* cited by examiner

*Primary Examiner*—Edward J. Glick
*Assistant Examiner*—Irakli Kiknadze

(57) ABSTRACT

A device and a method for the multispectral correction of radiation hardening in computer tomography with variable tube voltage is described. In particular, a water correction and a post-reconstructive hardening correction is disclosed. To perform the water correction, project image data is corrected, in that correction values are obtained from a previously determined correction table, by means of which a correction of the projection image data can be performed. By means of an image reconstruction, this produces a corrected volumetric image.

18 Claims, 8 Drawing Sheets

DEVICE AND METHOD FOR COMPUTER TOMOGRAPHY

CROSS REFERENCE TO RELATED APPLICATIONS

This application claims priority of German application No. 10 2005 028 216.4 filed Jun. 17, 2005, which is incorporated by reference herein in its entirety.

FIELD OF THE INVENTION

The invention relates to a device for computer tomography with:
a radiation source for x-raying an object to be examined from various projection directions,
a detector for detecting the radiation from the radiation source and
an evaluation unit downstream of the detector that corrects, with respect to radiation hardening, the projection images, taken by the detector, of an object to be investigated.

The invention also relates to a method for computer tomography.

BACKGROUND OF THE INVENTION

A computer tomographic device and a method for correcting the radiation hardening is known from DE 100 51 462 A1. The known device has an x-ray source and an x-ray detector that together rotate around an object to be examined. The projection images taken by the x-ray detector are applied to an evaluation unit that corrects the radiation hardening. To do this the evaluation unit performs a post-reconstructive correction procedure. As part of the post-reconstructive correction procedure, the evaluation unit first reconstructs approximate volumetric images from the object to be examined from the uncorrected projection images. The term volumetric image in this case, and in the following, means both three-dimensional volumetric views and two-dimensional section images. A reprojection is then performed, with only those pixels being used in the volumetric image whose the image value is above a specified threshold value and that are interpreted as materials to be distinguished from soft tissue. These materials can, for example, be bones or a contrast medium. The limitation to specific pixels enables the computing expense for the reprojection to be reduced.

With conventional computer tomography, a constant voltage is used for all projection directions, except for small fluctuations due to the generator for the tube voltage. The tube voltage is in this case preferably chosen so that the radiation dose received by the detector is adequate for all projection directions and object thicknesses. If the object to be examined is a patient, the patient under certain circumstances is exposed to a dose of radiation that is greater than would be necessary to take the particular projection image.

Devices and methods have therefore been developed to reduce as far as possible the radiation dose to which the patient is exposed. A device and a method of this kind are, for example, known from U.S. Pat. No. 6,222,907 B1. With the known device and known method, the parameters of the x-ray tube are controlled corresponding to the beam path through the object being examined.

The application areas for the known device and known method are radiography and fluoroscopy.

In recent times, the C-arch device for rotational angiography has been continuously improved. In particular, the mechanical stability of the C-arch has been increased, thus enabling approximate rotation about an isocenter. Together with the use of area detectors with an increased dynamic compared with x-ray image amplifiers, this enables a computer tomography volumetric reconstruction.

SUMMARY OF THE INVENTION

Starting from this prior art, the object of the invention is to provide a device for computer tomography with an optimized radiation dose and good image quality. The object of the invention is also to provide a method for the reconstruction of volumetric images from projection images.

These objects are achieved by a device and a method with the features of the independent claims. Advantageous embodiments and developments are given in associated dependent claims.

The device is especially characterized in that the radiation source used transmits radiation with different energy distributions in various projection directions depending on the absorption characteristics of the object to be examined, by adapting at least one operating parameter. The evaluation unit supplied with the value used at a specific projection direction reads, from a data memory, a correction value allocated to the value of the operating parameter and thus corrects the radiation hardening on the relevant projection image.

Accordingly, for a method for reconstructing volumetric images, an evaluation unit is supplied with at least one operating parameter together with projection image data, that is characteristic of the energy distribution of the radiation used to take the projection images. Furthermore, correction values for radiation correction relative to the value of the operating parameters, stored in a data memory, are read by the evaluation unit and the projection images are thus corrected with respect to radiation hardening.

Because the operating parameters of the radiation source determine the energy of the emitted radiation, the energy distribution of the radiation transmitted by the radiation source at known operating parameters is also known. It is thus possible to determine in advance the correction values for various values of the operating parameter, with which the radiation hardening can be corrected. The radiation hardening can thus be corrected in real time even with large amounts of data.

With a preferred form of embodiment, the radiation source is an x-ray source and the operating parameter the tube voltage of the x-ray source. Then, by means of the value of the tube voltage, the energy distribution, for a known material composition of the anode, of the x-ray photons emitted from the anode is known.

With a further preferred form of embodiment, the evaluation unit performs what is called a water correction in that the evaluation unit determines, at a specific image value, a correction value stored in a data memory and relative to both the image value and the tube voltage. In this case it assumed for simplification that the attenuation of the radiation is caused by water-equivalent material.

Furthermore, the evaluation unit can also perform a post-reconstructive correction for radiation hardening relative to the tube voltage. To do so, the evaluation unit generates a three-dimensional object model, differentiated according to absorption characteristics, and allocates to the image values object data records derived in each case from the object model. Furthermore, the evaluation unit reads out from a data memory the correction values allocated to the object data records and the tube voltage, and thus performs the correction of the radiation hardening.

To reduce the computing expense, the evaluation unit preferably performs the correction of the radiation hardening with a spatial resolution that is less that the spatial resolution of the projection images. This is generally sufficient because the artifacts in the reconstructed volumetric images induced by the radiation hardening generally have low spatial frequencies.

BRIEF DESCRIPTION OF THE DRAWINGS

Further details and advantages of the invention are given in the following description, in which exemplary embodiments of the invention are explained in detail using the accompanying drawings. These are as follows.

DETAILED DESCRIPTION OF THE INVENTION

Figure 1:
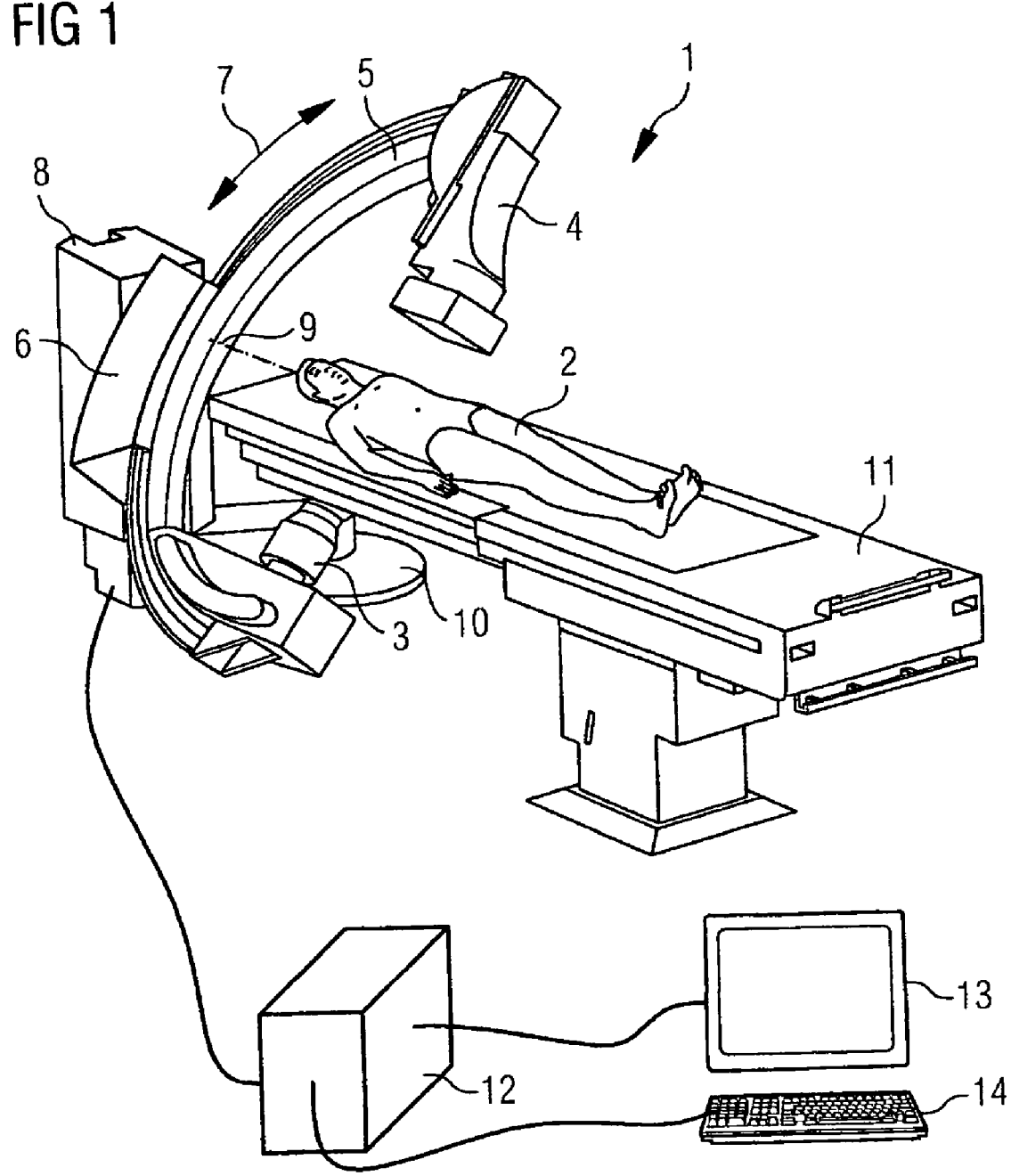
FIG. 1 A perspective view of a computer tomography unit with a C-arch.

FIG. 1 shows a perspective view of an x-ray system 1 that can be used for rotational angiograph y. The x-ray system 1 enables the computer-tomographic volumetric reconstruction of the inner structure of a patient 2. The x-ray system 1 includes an x-ray tube 3 and a detector 4, that detects the x-ray radiation transmitted from the x-ray tube 3. On the way to the detector 4 the x-ray radiation passes through the patient 2 so that the detector 4 takes projection images of the patient 2. The detector 4 is preferably a digital area detector.

The x-ray tube 3 and detector 4 are mounted on a C-arch 5 that is secured by a mounting 6. The C-arch 5 is supported in the mounting 6 in such a way that it can move in a circumferential direction 7. The mounting 6 is fitted to a stand 8 so that it can rotate about a rotary axis 9. The stand 8 is secured to a floor mounting 10 that enables the stand 8 to move.

When the x-ray system 1 is operating, the C-arch 5 rotates about the rotary axis 9 and thus passes around a patient couch 11, on which the patient 2 is supported.

The detector 4 is connected to an evaluation unit 12 that calculates a volumetric image of the inner structure of the patient 2 from the projection images taken by the detector. The volumetric image can, for example, be displayed on a monitor 13. Connected to the evaluation unit 12 are mainly input devices 14 by means of which the x-ray system 1 can be controlled.

In the case of conventional devices for high-speed computer tomography, the x-ray detector and the x-ray radiation source rotate around the object to be examined at high speed in a fixed frame. Compared with this, the x-ray tube 3 and detector 4 on the x-ray system 1 move relatively slowly. Control of the tube voltage U matched to the dimensions of the object to be examined therefore appears relatively easy to accomplish.

Figure 2:
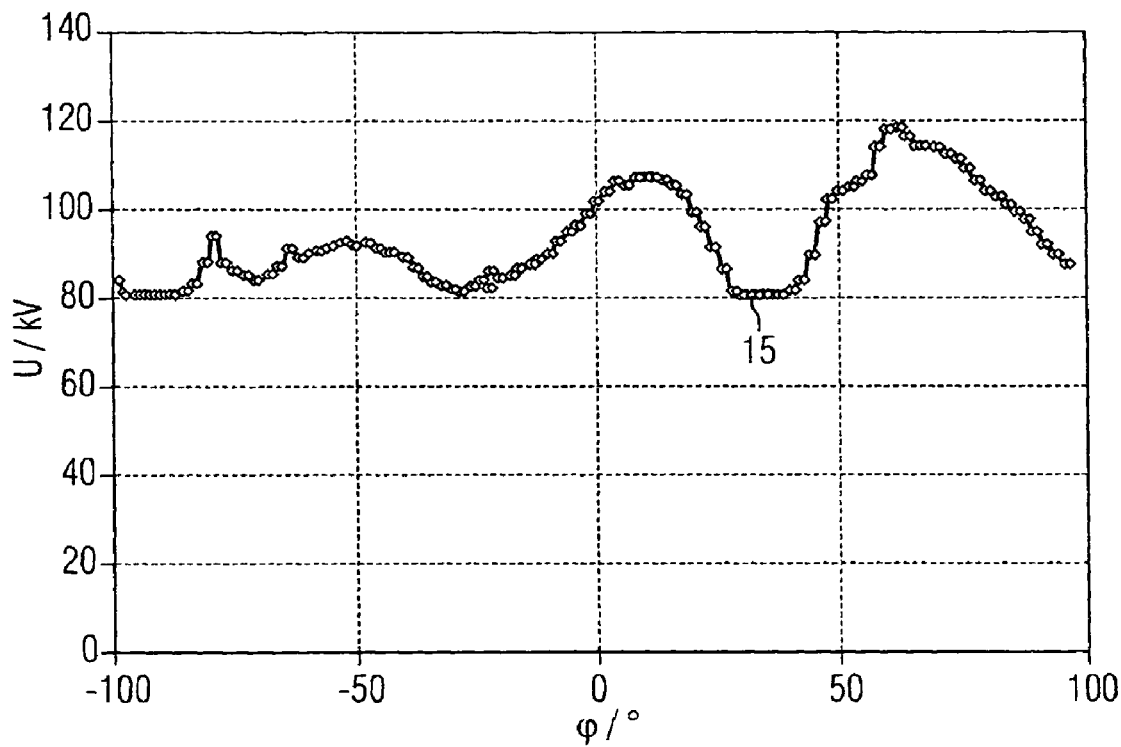
FIG. 2 A diagram showing the change in tube voltage of an x-ray source compared with the projection angle.

FIG. 2 shows a voltage curve 15 of the typical pattern of the tube voltage U for a rotational angiograph image of the heart. In this case, the C-arch 5 is, for example, moving over an angular range of 200 degrees from the left anterior oblique position 100 to the right anterior oblique position 100. During the movement of the C-arch 5, 200 projection images are, for example, taken. To be able to compensate for the different attenuation at different projection angles φ the parameters of the tube voltage, x-ray pulse width and tube current are dynamically matched during the rotation of the C-arch 5. For thorax rotational images, the tube voltage U can vary completely in the range between approximately 70 kV for anterior posterior radiation and 125 kV for lateral imaging through the shoulder area.

Voltage-Dependent Radiation Hardening

Figure 3:
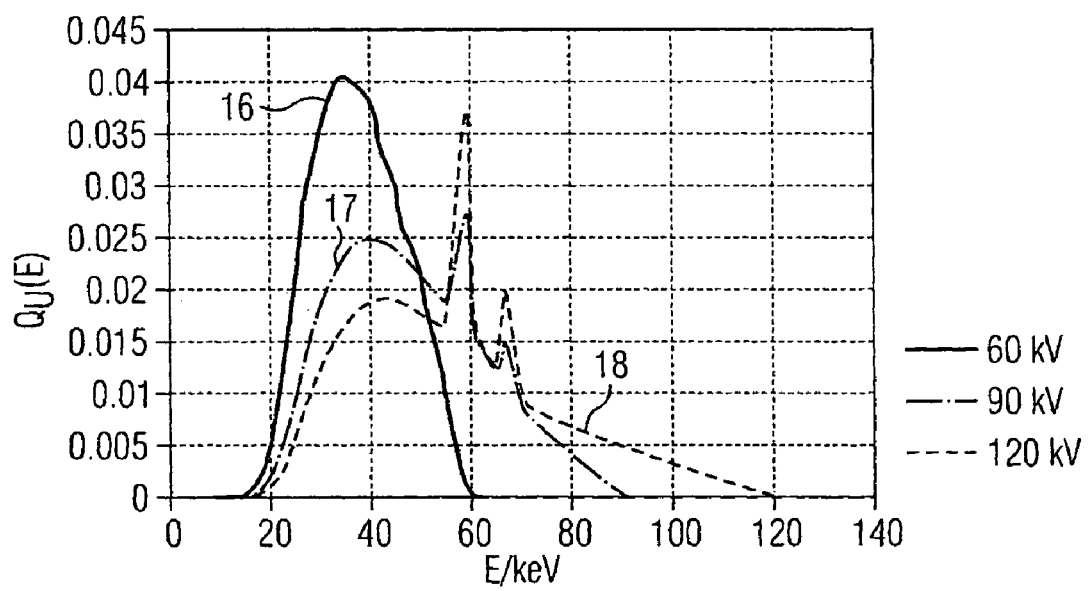
FIG. 3 A diagram showing the spectra of an x-ray radiation emitted by a tungsten anode at different tube voltages.

The radiation of x-ray tube 3 is also polychromatic. The energy spectrum of the photons emitted as braking radiation at the anode depends mainly on the applied tube voltage U, with which the electrons can be accelerated from the cathode to the anode. At a tube voltage U, it is usually a high voltage in the kV range. The maximum photon energy is then $$E_{max}(U) = U(\text{keV}/\text{kV}) = eU,$$

with kilo electron volts (keV) usually being used as the unit of energy. Some typical emission spectra $Q_U(E)$ for various voltages are shown in FIG. 3, in the emission spectra 16, 17 and 18 the pattern of the emission spectrum $Q_U(E)$ in each case is shown at a tube voltage of 60 kV, 90 kV and 120 kV. It should be noted that the anode of the x-ray tube 3 is manufactured of tungsten and the radiation emitted from the anode is internally filtered through a 2.5 mm thick wall of aluminum.

However, the emission spectrum alone does not determine the imaging, but also the transparency of the spectral filters used $$W(E) = \exp(-\mu(E)T)$$

with energy-dependent attenuation coefficient $\mu(E)$ and thickness T The spectral response sensitivity $\eta_D(E)$ of the detector is also determinant for the imaging.

The resulting effective standard spectral distributions $S_U(E)$ are therefore defined by:

$$S_U(E) = Q_U(E)W(E)\eta_D(E)/c_U \qquad (\#1)$$

with the standard factor:

$$c_U = \int_0^{eU} Q_U(E)W(E)\eta_D(E)dE, \Rightarrow \int_0^{eU} S_U(E)dE = 1.$$

Figure 4:
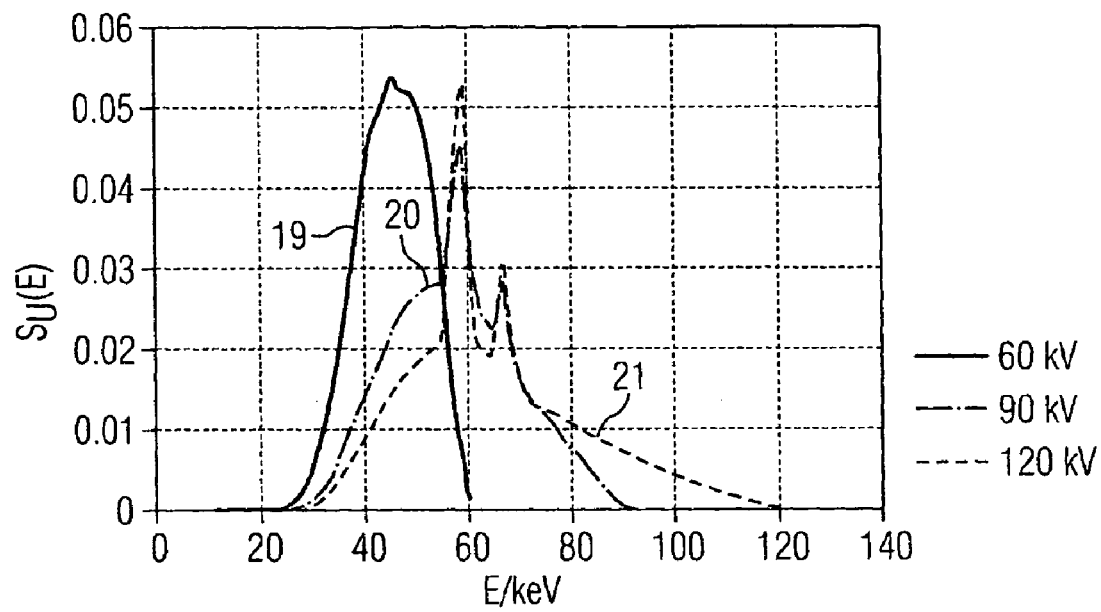
FIG. 4 A diagram showing the effective spectra ascertained by an x-ray detector at different tube voltages.

Examples of effective spectral distributions $S_U(E)$ are shown in FIG. 4, where various resulting spectral distributions $S_U(E)$ that originate from emission spectra 16 to 18 when considering additional filters and the detector response sensitivity of the detector 4 are recorded. In particular, the emission spectra 16, 17 and 18 each lead to spectral distribution 19, 20 and 21. For the case shown in FIG. 4, a filter of copper 0.3 mm thick was used and the detector was a CsI scintillator detector 0.55 mm thick with a density of 3.6 grams per cubic cm.

Figure 5:
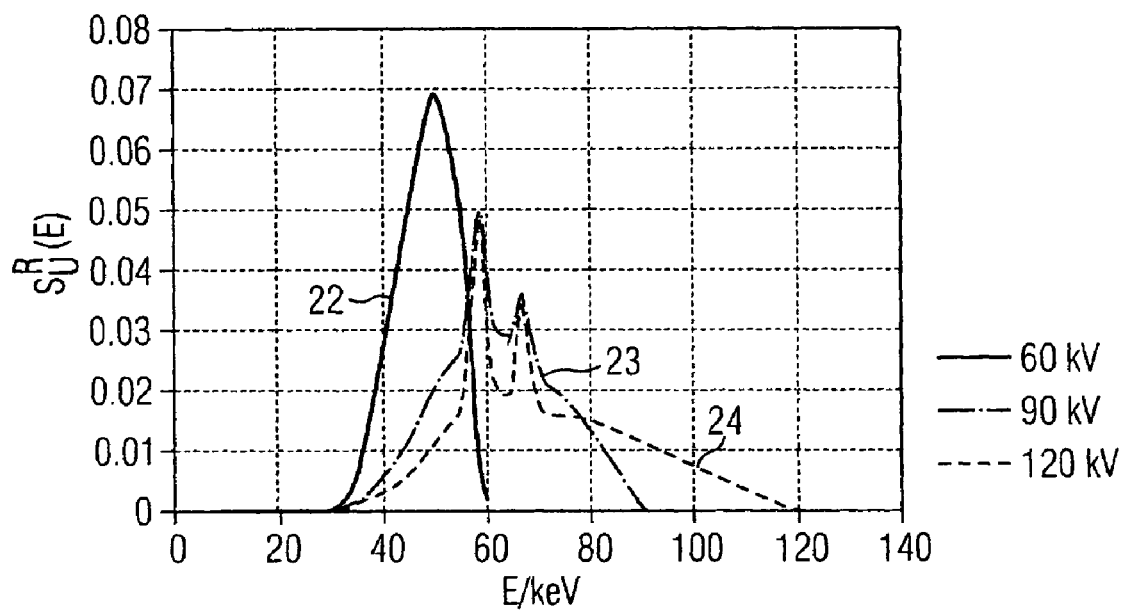
FIG. 5 A diagram showing the spectra resulting when twenty centimeters of water are x-rayed.

Furthermore, during the penetration through matter the number of low-energy photons is reduced more severely by absorption or scatter than the number of high-energy photons, which leads to a radiation hardening depending on the material and path length. For example, the dominance of photons of higher energies in the resulting spectral distribution $S_U^R(E)$ can be seen in FIG. 5. In FIG. 5, the resulting spectral distributions 22, 23 and 24 originating from the resulting spectral distributions 19, 20 and 21 during the passage through 20 cm of water are shown. A comparison with FIG. 4 clearly shows that the resulting spectral distributions 19, 20 and 21 from FIG. 4 have been attenuated at the low-energy end when passing through 20 cm of water.

This phenomenon of radiation hardening occurs with objects made of homogenous material. With a cylindrical cross-section of water, for example, with a radiation passage transverse to the longitudinal axis the radiation hardening at the edge is less than in the area of the center of the cylinder where the radiation has to cover a long path through the cylinder.

However, the theory of reconstruction of volumetric images presumes monochromatic radiation. Ignoring polychromacity leads, for example, to something called the cupping effect after the reconstruction, i.e. the reconstructed attenuation coefficient (gray value) reduces continuously from the edge inwards. This effect can be relatively easily corrected for materials of a lower atomic number, that are similar to water, such as soft tissue, fat and many plastics. The expression water correction or first order hardening correction is used.

Furthermore, the radiation hardening is intensified by the presence of materials with high atomic numbers, particularly by bones, contrast media or metal implants. Local density distortions occur after the reconstruction even after water correction, particularly bar or shadow-type artifacts, for example between heavily absorbent bone structures. Such second order hardening artifacts 2 can reach an intensity of 10 to approx 100 HU (Hounsfield unit, corresponding to 0.1 percent of the attenuation coefficient of water). The cause is ultimately the energy dependency of the attenuation coefficients for materials with a higher atomic number that deviates strongly from water. The correction of this effect is referred to in the following as second order hardening correction.

Figure 6:
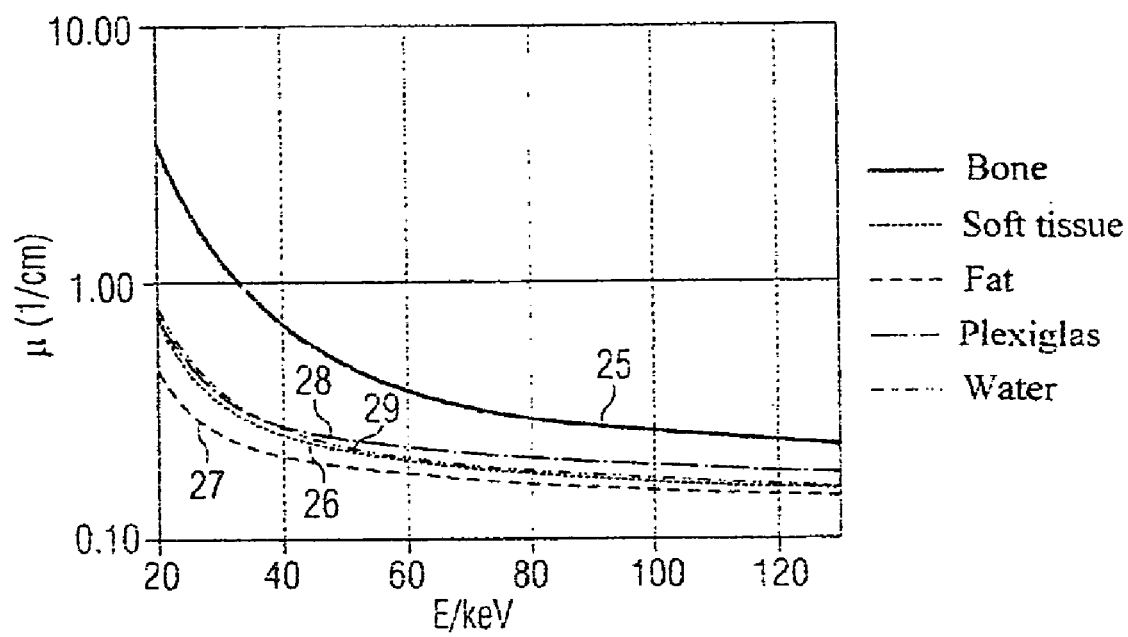
FIG. 6 The relationship of the attenuation coefficients of various materials to the energy of x-ray photons.
Figure 7:
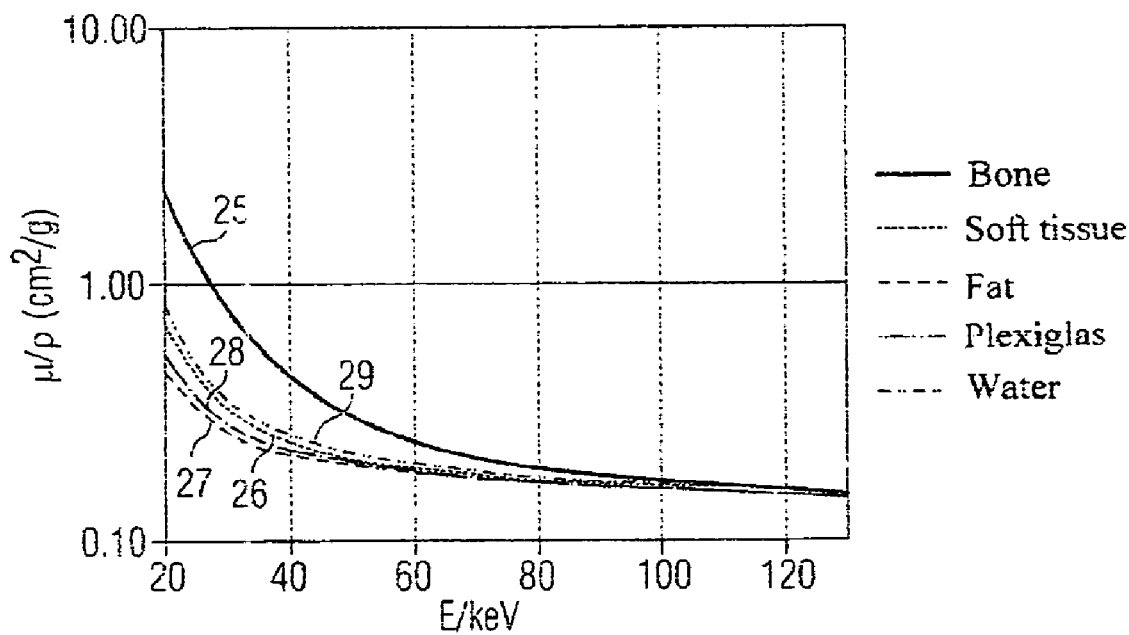
FIG. 7 An illustration of the relationship of the mass attenuation coefficients of various materials to the energy of x-ray photons.

The dependency of the attenuation coefficient on the photon energy is shown in FIGS. 6 and 7 for various materials. FIG. 6 shows the dependence of the linear attenuation coefficient $\mu$ on the photon energy, whereas FIG. 7 shows the dependency of the mass attenuation coefficient $\mu/\rho$. An attenuation curve 25 represents the attenuation through bony tissue. The attenuation curve 25 for bony tissue is distinctly above an attenuation curve 26 for soft tissue, above an attenuation curve 27 for fatty tissue, an attenuation curve 28 for Plexiglas and an attenuation curve 29 for water. What is striking in FIG. 6 is that the attenuation curve 26 for soft tissue is almost exactly the same as the attenuation curve 29 for water. The mass attenuation coefficient shown in FIG. 7 shows that the differences between bony tissue on the one hand and soft tissue, fatty tissue and water on the other is even more distinct. In this case, the attenuation curve 25 for bone is clearly raised above the other attenuation curves 26 to 29, that lie comparatively close together.

Multispectral Water Correction: Preconstructive First Order Radiation Hardening Correction For simplicity, when considering water correction or first order hardening correction the attenuation of an x-ray photon beam in the object to be examined, that is usually a patient 2, is caused solely by water-equivalent material. In this case water equivalence means that it is assumed that the energy dependency of the mass attenuation coefficient $(\mu/\rho)(E)$ is identical to water and differences are due only to local differences in density. Accordingly, muscle tissue, blood or also bony tissue is treated as water with a higher density $(\rho > 1 \text{ g/cm}^3)$ We now consider a measuring beam that penetrates the object to be examined. Let the coordinate along its path be x and the local (linear) energy-dependent attenuation coefficient $$\mu(x,E) = \rho(x)\alpha(x,E),$$

with the mass attenuation coefficient being shortened with $\alpha$:

$$\alpha(x,E) = \mu(x,E)/\rho(x).$$

The polychromatic logarithmic CT projection value for the measuring beam under consideration is then $$\tilde{p} = -\log\left(\int_0^{eU} \exp\left(-\int \mu(x,E)dx\right)S_U\,dE\right) \qquad (\#2)$$

$$= -\log\left(\int_0^{eU} \exp\left(-\int \rho(x)\alpha(x,E)dx\right)S_U\,dE\right)$$

with the measuring beam belonging to a projection number j, recorded at a tube voltage $U = U_j$.

For this purpose, an equivalent water density $b_U = b_U(\tilde{p})$ is determined in the following manner: let $\alpha_W(E)$ be the energy-dependent mass attenuation coefficient of water, then the polychromatic logarithmic projection value for a measuring beam with a voltage-dependent spectral distribution $S_U(E)$, that is attenuated along a path length (coverage density) b in water $(\rho = 1 \text{ g/cm}^3)$ is determined as:

$$f_U(b) = -\log\left(\int_0^{eU} \exp(-b\alpha_W(E))S_U\,dE\right) \qquad (\#3)$$

Figure 8:
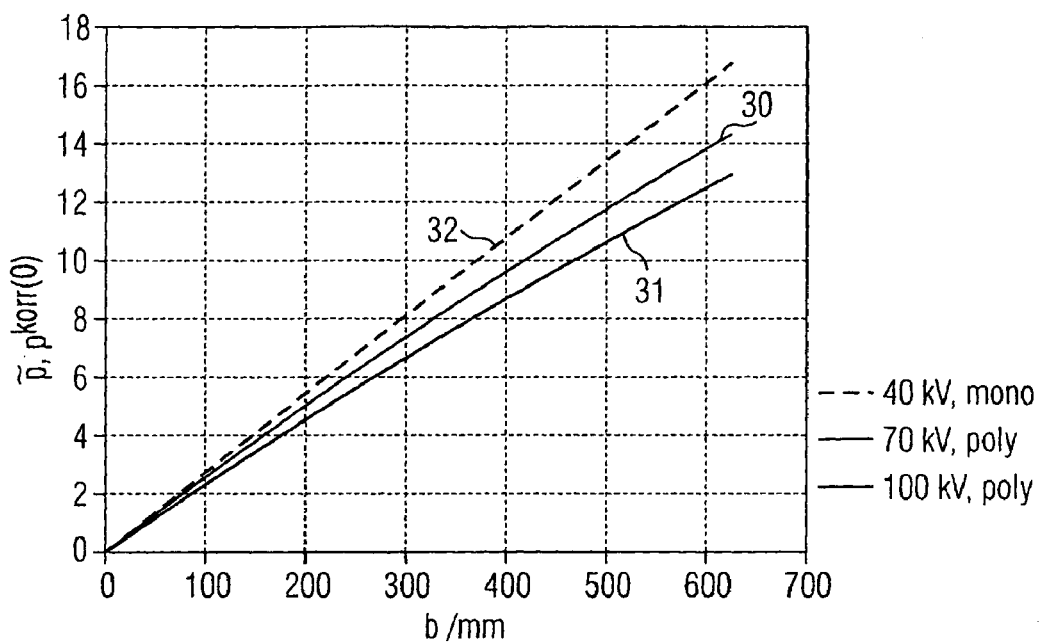
FIG. 8 A diagram showing the relationship between projection values simulating passage through water and the path length for various tube voltages.

This function can be calculated in advance for every voltage U or also experimentally determined. In FIG. 8, the functions $f_U$ are shown as projection value curves 30 and 31 for the tube voltage relative to various voltage values. The projection value curve 30 shows the relationship between the polychromatic logarithmic projection value p̃ depending on the path length b at a tube voltage of 70 kV, and a projection value curve 31 shows the relationship between the polychromatic logarithmic projection value p̃ and the path length b at a tube voltage of 100 kV. The projection value curves 30 and 31 rise monotonously with b and can be inverted. This preferably takes place numerically, for example by means of an inverse interpolation.

For each measured value p̃ in accordance with equation (#2) an equivalent water density $b_U = b_U(\tilde{p}) = b$ can be determined so that $\tilde{p} = f_U(b)$ applies in accordance with equation (#3), i.e. by inversion of equation (#3):

$$b_U = f_U^{-1}(\tilde{p}) \tag{#4}$$

with $b_U$ it is then possible to convert to the corresponding projection value, that ideally would have been measured at a monochromatic spectrum with photons with only a single reference energy $E_0$. With $b_U$ according to equation (#4) the corrected water-equivalent monochromatic logarithmic project value results $$p^{korr(0)} = \alpha_W(E_0) b_U = \alpha_W(E_0) f_U^{-1}(\tilde{p}) = F_U(\tilde{p}) \tag{#5}$$

In FIG. 8 a projection value curve 32 represents the pattern of the equivalent monochromatic logarithmic projection value $p^{korr(0)}$ at a photon energy $E_0$ of 40 kV.

The water correction can be illustrated using FIG. 8. With the measured projection value p̃, the associated $b_U$ is sought using the projection value curve 30 or 31 matching the tube voltage. With the value for $b_U$, the corrected monochromatic projection $p^{korr(0)}$ can then be sought by using the projection value curve 32.

It should be noted that in fact the conversion $\tilde{p} \to p^{korr(0)}$ depends on the voltage U. With the homogenous material, water, and the fixed specified path b, a constant path length $b_U = b$ is, however, obtained from the inversion of the equation (#4) and a constant monochromatic projection value $p^{korr(0)}$ from the equation (#5), that in each case is independent of U.

Figure 9:
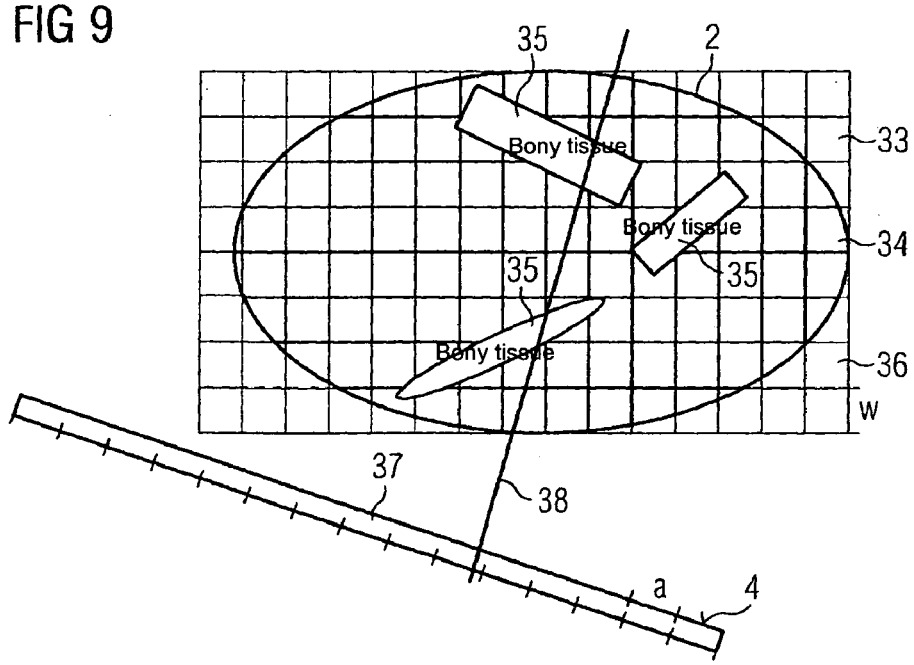
FIG. 9 A cross-section through an object to be examined and a flat image detector for illustrating the material-selective reprojection.

It should also be noted that the right-hand sides of equations (#2) and (#3) are identical if the measuring beam penetrates a thickness b in water. Then in the equation (#2) we get $b = \int \rho(x) dx$ and $\alpha(x,E) = \alpha_W(E)$ Multispectral, Material-Selective Post-Reconstructive Hardening Correction: Second Order Hardening Correction Following the illustration of the first order hardening correction, that is used directly on the projection data, a description of a multispectral, material-selective, second order hardening correction is now described using FIG. 9. The second order hardening correction is based on an iterative post-reconstructive correction approach, whereby the physical process of the spectral hardening is remodeled using an already reconstructed, but not yet adequately corrected, volumetric image 33. A material-selective segmentation is applied to the existing volumetric image 33, which is usually a three-dimensional volumetric dimension image 33, by means of threshold criteria. FIG. 9 shows the segmentation of the volumetric image 33. For simplicity, FIG. 4 shows only the cross-section through the three-dimensional volumetric image 33. The volumetric image 33 contains structure data of a patient 2, the outer contours of whom are shown by an ellipse in FIG. 9. Within the patient 2 is, in addition to soft tissue 34, also bony tissue 35. Furthermore, vessels filled with contrast media or metal implants can also be present. The volumetric image 33 is made up of individual volumetric elements 36, known as voxels. The individual voxels are allocated to the categories soft tissue 34 or bony tissue 35 and to other categories as appropriate, depending on the gray values. The volumetric image 33 is then projected on pixel 37 of the detector 4. In doing so, the mass coverage in grams per square centimeter for the soft tissue 34 and bony tissue 35 along a measuring beam 38 allocated to the particular pixel 37 is determined.

From the reprojection after the segmentation we then get, for each individual measuring beam 38, a value tuple for the coverage thickness with a density*path length unit in g/cm² of the various segmented material along the measuring beam 38 through the object volume.

The following explanations are, without restricting the generality, limited for simplicity to two materials with coverage thicknesses $b_W$ and $b_K$. By access to tables, generally followed by interpolation, a correction factor is then allocated to the value pair ($b_W$, $b_K$) for conversion of polychromatic projection data, disturbed by the hardening effect, into monochromatic projection data.

The multiparameter correction Table C, that is broken down into fine discreet steps relative to $b_W$ and $b_K$ and still depends on the tube voltage U, can then be calculated in advance as follows before taking an image using the x-ray system 1, or if necessary also determined by measurements or adapted:

$$C_U(b_W, b_K) = g^{(0)}(b_W, b_K, E_0) / g_U(b_W, b_K) \tag{#6}$$

In this case, $g^{(0)}$ and $g_U$ are the logarithmic mono- and polychromatic projection values, defined by $$g^{(0)}(b_W, b_K, E_0) = b_W \alpha_W(E_0) + b_K \alpha_K(E_0) \tag{#7}$$

$$g_U(b_W, b_K) = -\log \left( \int_0^{eU} \exp(-b_W \alpha_W(E) - b_K \alpha_K(E)) S_U \, dE \right) \tag{#8}$$

The comparison with equation (#3) shows that the following applies:

$$f_U(b) = g_U(b, 0) \tag{#9}$$

The hardening correction of the polychromatic measured projection data p̃ then takes place by multiplication with a correction factor $C_U$ $$p^{korr} = C_U(b_W, b_K) \tilde{p} \tag{#10}$$

or by addition $$p^{korr} = \tilde{p} + \delta p^{(1)} \tag{#11}$$

with the correction projection data $$\delta p^{(1)} = (C_U(b_W, b_K) - 1) \tilde{p} \tag{#12}$$

It is noted that the corrections depend on the voltage $U = U_j$ used in the particular projection No. j. The corrected projection data or the correction projection data is used for a new volumetric image reconstruction. The correction cycle can then be iteratively repeated with a new segmentation, with a new determination of material-specific coverages $b_W', b_K'$ by segmented reprojection, new correction in accordance with equations (#10) and (#11)-(#12) and with a new reconstruction.

Two-Stage Correction: Multispectral First and Second Order Hardening Correction

It is pointed out that for the actual implementation in the x-ray system 1 the correction (#11), $\tilde{p} \to p^{korr}$, is not performed in one step, but instead the water correction is carried out first. This operates directly on the projection data and requires no reprojection. Only then is the deviation from the water correction, as a second order correction, corrected. The segmented reprojection is then required for this:

First order correction: $\tilde{p} \rightarrow p^{korr(0)}$ according to (#5)

Second order correction: $p^{korr(0)} \rightarrow p^{korr} = p^{korr(0)} + \delta p^{(2)}$ (#13)

$$\delta p^{(2)} = (C_U^{(2)}(b_W, b_K) - 1)p^{korr(0)} \quad (\#14)$$

$$C_U^{(2)}(b_W, b_K) = C_U(b_W, b_K)\frac{\tilde{p}}{p^{korr(0)}} \quad (\#15)$$

The corrections depend, as mentioned, on the voltage $U=U_j$ used in the particular projection No. j. The correction procedure can be iteratively continued.

Reduction of the Computing Expense of the Post-Reconstructive Corrections

There are various methods of keeping the computing expense low. In DE 100 51 462 the fact that the non-water-similar hardening materials with a higher atomic number, for example, bones, contrast media or metal usually have only a fraction of pixels 37 or voxels 36 is utilized by clever data organization.

Furthermore, it is possible to subject only correction projection data, corresponding to $\delta p^{(1)}$ or $\delta p^{(2)}$, to a new volumetric image reconstruction, in order to calculate a correction volumetric image and only then superimpose it by addition to the uncorrected volumetric image. This essentially uses the linearity of the image reconstruction because the linearity enables the sequence of addition and reconstruction to be switched.

Both methods of expense reduction can be combined.

In the following, a detailed description of the performance of the hardening correction is described with the aid of FIGS. 10 to 12. The hardening correction taking place in the evaluation unit 12 can be implemented both in the software and in the hardware. In the following, block diagrams that reflect the sequence are described and also pseudocode is given.

Multispectral Water Correction

Figure 10:
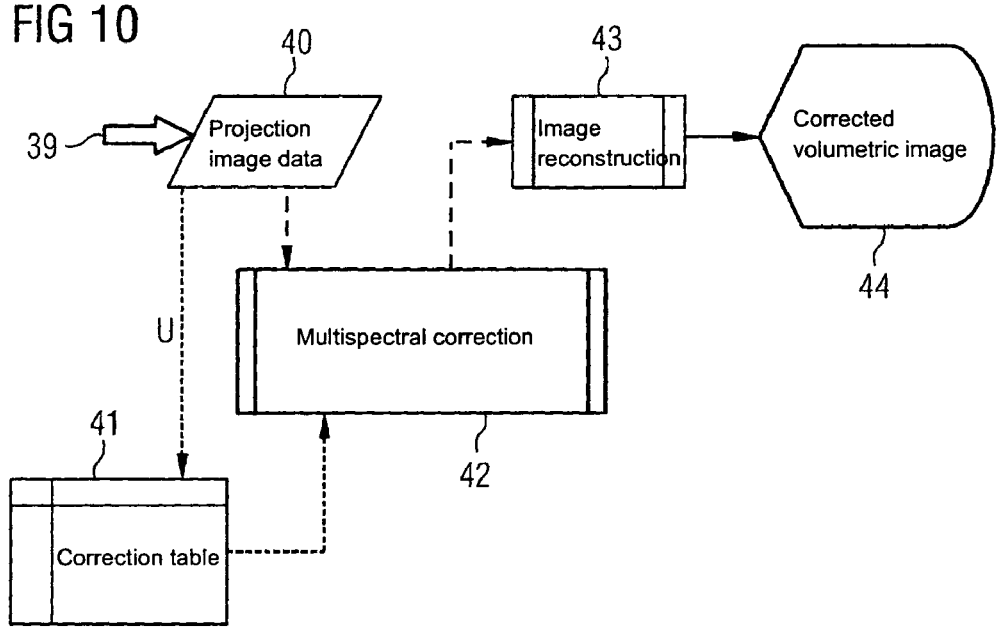
FIG. 10 A block diagram for illustrating the sequence of a first order revaluation correction, known as the water correction.

FIG. 10 shows the sequence of a water correction carried out by the evaluation unit 12.

First, a data acquisition 39, that leads to projection image data 40, is performed with the aid of the detector 4. The projection image data 40 also contains the particular tube voltage U used of the x-ray tube 3. Using the correction table 41 applicable for the tube voltage U in which the corrected projection values are entered relative to the measured projection values, a multispectral correction 42 of the beam revaluation is carried out. The correction 42 depends on the actual tube voltage U of the x-ray tube 3. Using the corrected projection image data, an image reconstruction 43 is then carried out, leading to a volumetric image 44 with the radiation hardening due to water or body parts of the patient 2, that have similar absorption properties to water, being corrected.

In the following, the process of water correction is described again by pseudocode.

When doing so, it is assumed that the (two-parameter) water correction family of tables $F_U(p)$ for the voltage range $U_{min} \leq U \leq U_{max}$, used for system control and calculated in advance with suitable discretization $U=U_n=U_{min}+(n-1)\Delta U$, $n=1,2,\ldots$, is available (for example $\Delta U=5$ kV).

The pseudocode is then:

for each projection direction j=1,N with a projection angle $\phi_j = \phi_0 + (j-1)\Delta\phi$ and tube voltage $U_j$:
load table $F_U(\ )$ with $U=U_j$ or interpolated table from $F_U(\ )$ and $F_{U'}(\ )$ with $U=U_n \leq U_j < U'=U_{n+1}$;
read projection image $\tilde{p}=(\tilde{p}_{kl})$, whereby k,l are pixels indices of the projection image for projection No. j;
for each projection image pixel (k,l):
water correction according to equation (#5) using table $F_U(\ )$: $\tilde{p}_{kl} \rightarrow F_U(\tilde{p}_{kl})$
for the corrected projection image $p^{korr(0)}=(F_U(\tilde{p}_{kl}))$:
image reconstruction updating (additive superimposition in the reconstruction volume)

It is pointed out that the image reconstruction is not limited to the Feldkamp algorithm, under certain circumstances with Parker weighting, at projection angles of less than 360 degrees. There are generalizations that are still back projections filtered from the type. Furthermore, every suitable reconstruction algorithm can, in principle, be used, for example also a reconstruction method of the algebraic iterative reconstruction type.

Iterative, Multispectral, Second Order Hardening Correction

Figure 11:
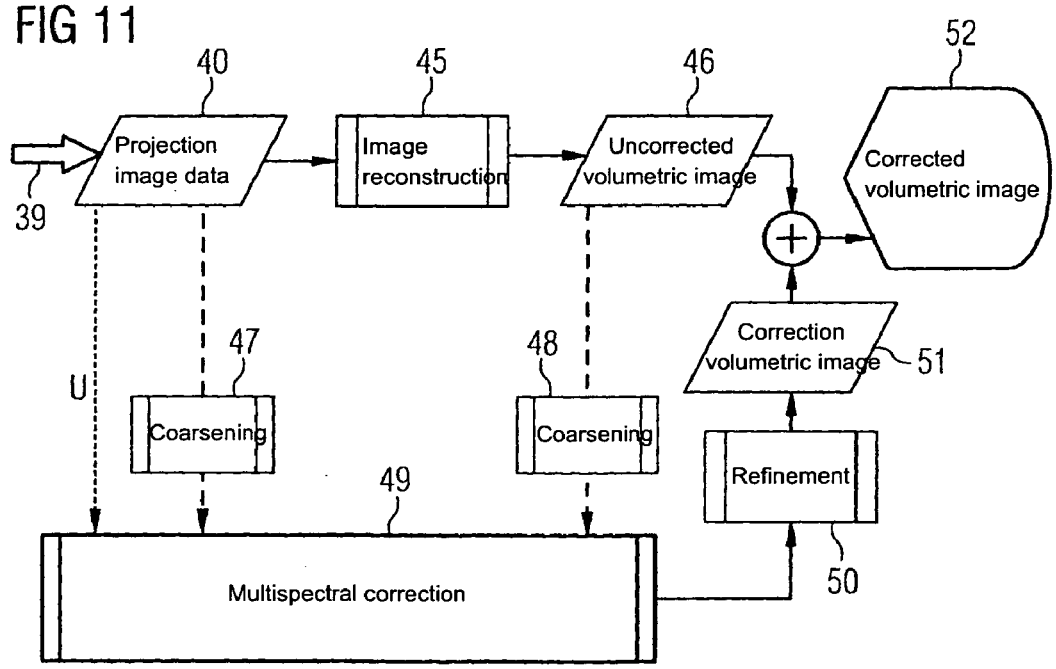
FIG. 11 A block diagram to illustrate the sequence of a second order iterative multispectral revaluation correction.

FIG. 11 is a flow diagram of an iterative, multispectral second order correction of the beam hardening.

As for the water correction described using FIG. 10, the data acquisition 39 leads to projection image data 40. Using the projection image data 40, an image reconstruction 45 was carried out that leads to an uncorrected volumetric image 46. The original projection image data 40 and the uncorrected volumetric image 46 are each subjected to coarsening 47 and 48, with the spatial resolution of the original projection image data 40 and uncorrected volumetric image 46 being reduced. Using the data obtained in this way and the values for the tube voltage U, a multispectral correction 49 of the radiation hardening is then carried out, with the relevant allocated tube voltage U being taken into account for the projection images.

By means of a succeeding refinement 50 of the correction volume image supplied from the correction 49, a correction volumetric image 51 is generated that is added to the uncorrected volumetric image 46 and a corrected volumetric image 52 thus results. As part of the refinement 50, the spatial resolution of the correction volumetric image is increased by interpolation corresponding to the spatial resolution of the uncorrected volumetric image 43.

In principle, the coarsening 47 and 48 and refining 50 steps can be omitted. This does, however, lead to a higher computing cost.

Figure 12:
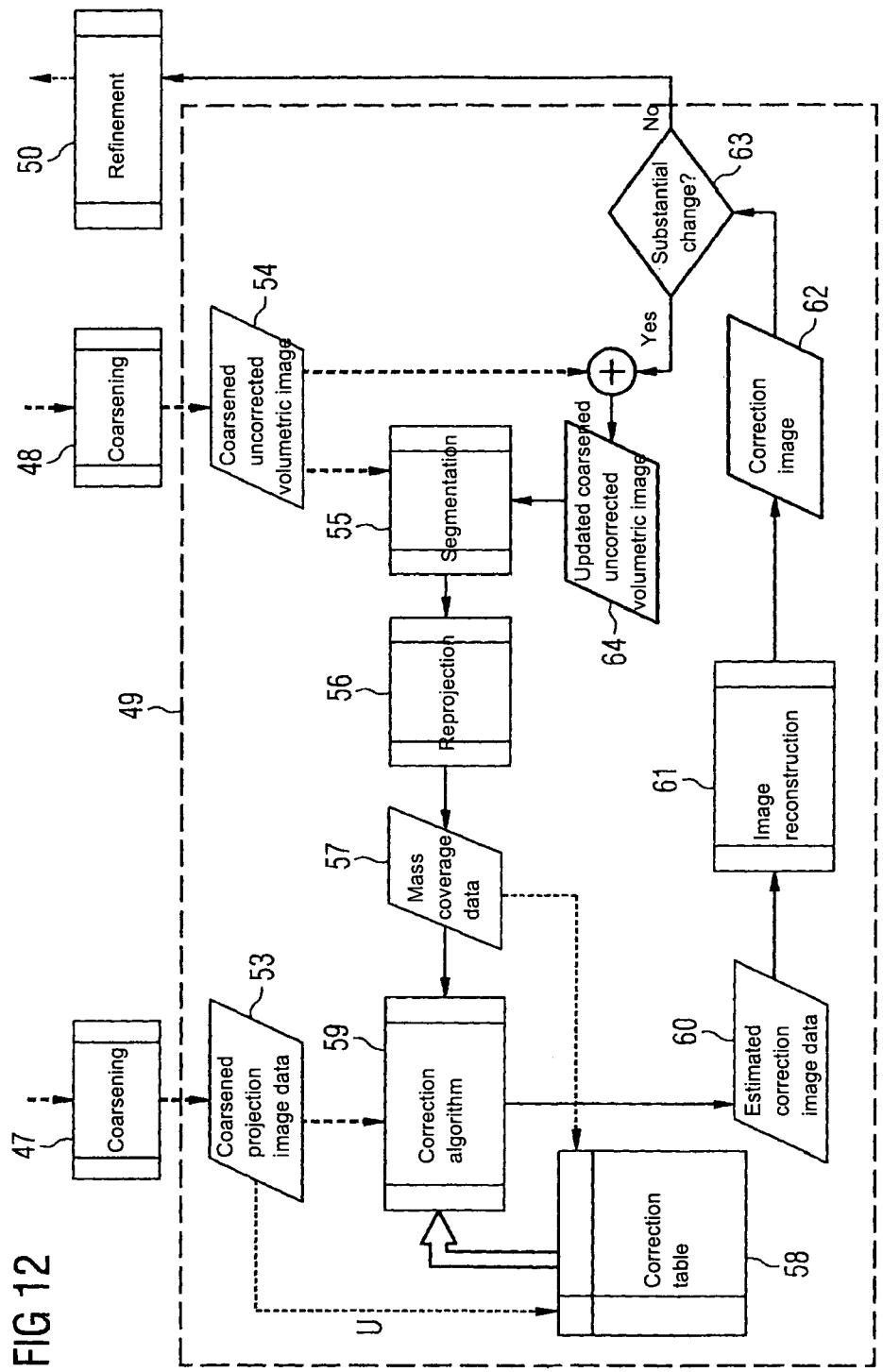
FIG. 12 A block diagram showing details of the second order iterative multispectral hardening correction from FIG. 11.

FIG. 12 shows the details of the correction 49 from FIG. 11. The coarsening 47 of the uncorrected projection image data 40 leads to coarsened projection image data 53 and the coarsening 48 to a coarsened uncorrected volumetric image 54. A segmentation 55 in accordance with FIG. 9 is carried out using the coarsened uncorrected volumetric image 54 and this is followed by a reprojection 56 that produces the mass coverage data 57, for example $(b_K, b_W)$. Depending on the tube voltage U and mass coverage data 57, a correction table 58 is consulted that contains the correction values $C_U(b_K, b_W)$ relative to the tube voltage U for conversion of polychromatic projection values into monochromatic projection values. With this correction data from the correction table 58, a correction algorithm 59 is used that processes the coarsened projection image data 53 and from this generates estimated correction projection image data 60. Using the estimated correction image data 60, a reconstruction 61 is performed that leads to a correction image 62 with less spatial resolution. A subsequent question 63 is then asked to determine whether the correction image 62 has substantially changed in the last iteration step. If a substantial change is present, the correction image 62 is added to the coarsened uncorrected volumetric image 54 and the segmentation 55 is performed again. This is followed by a new reprojection 56 to generate improved mass coverage data 57, followed by consultation of the correction table 58 and performance of the correction algorithm 59 again, that leads to improved, estimated correction projection image data 60. The reconstruction 61 can then be repeated, so that an improved correction image 62 results.

If the correction image 62 has not substantially changed, the refining 50 is carried out, leading to the correction volumetric image 51 with the original spatial resolution.

The process of a second order hardening correction again using pseudocode is described in the following.

It is again assumed that the (three or more parameter) family of hardening correction tables $C_U( )$ according to equation (#6) is available, calculated in advance with suitable discretizing, for the voltage range $U_{min} \leq U \leq U_{max}$ used for the system control.

Figure 13:
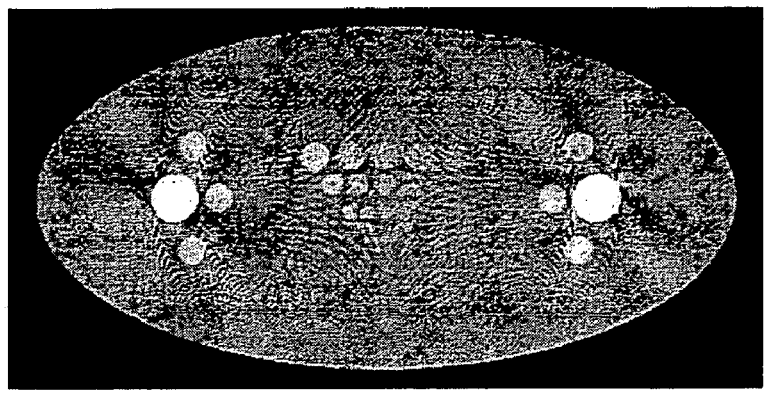
FIG. 13 The representation of the reconstruction of an object, with the reconstruction being performed assuming constant tube voltage and using projection images that have been taken using variable tube voltage.
Figure 14:
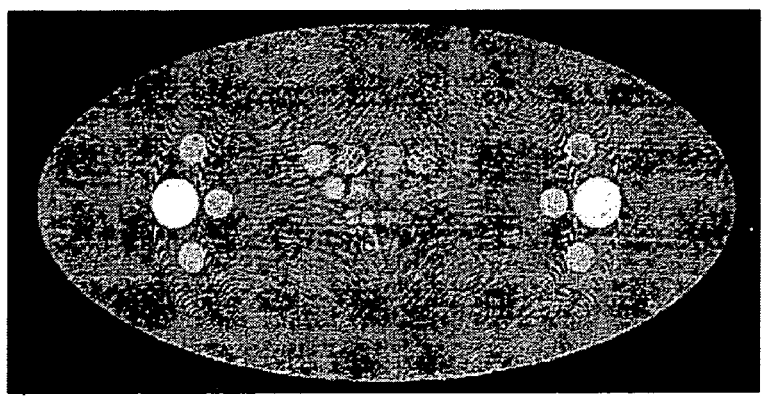
FIG. 14 The representation of the reconstruction of the object from FIG. 13, taking account of voltage changes.

The pseudocode is then:
first volumetric image reconstruction with the aid of a standard reconstruction
volumetric image segmentation with material-selective threshold values
calculate the material-selective, hardening corrective volumetric image as follows:
for each projection direction j=1,N with a projection angle $\phi_j = \phi_0 + (j-1)\Delta\phi$ and tube voltage $U_j$:
load multiparameter, hardening correction table $C_U$ with $U=U_j$ or interpolated table from $C_U$ and $C_{U'}$ with $U=U_n^j \leq U_j < U' = U_{n+1}$;
read projection image $\tilde{p} = (\tilde{p}_{k,l})$ with k,l being pixel indices for the projection image for projection No. j
for each projection image pixel (k,l) and the measuring beam striking this pixel:
segmented (material selective) reprojection from which coverage thicknesses $b_W, b_K, \ldots$ result
hardening correction projection value according to equation (#12) using the look-up table $C_U$: $\tilde{p}_{k,l} \rightarrow p^{(1)}_{k,l}$
for the correction projection image $\delta p^{(1)} = (\delta p^{(1)}_{k,l})$: filtered reprojection
image reconstruction updating (additive superimposition in the reconstruction volume)
adding the hardening correction volumetric image as a superimposition to the standard reconstruction volumetric image
Iteration (optional): Repeat steps 1 * to 3*
    Simulation Calculations The method described here was tested in the simulation calculations. During the simulation calculations, a heavily simplified femur phantom with low contrast inserts was used. FIG. 13 shows a cross-section through a reconstructed volumetric image that was taken using variable voltage, but with the hardening correction having been performed assuming a constant voltage. FIG. 14 shows the same cross-section that results if the variability of the tube voltage is taken into account when correcting the hardening in accordance with the method described here.

Figure 15:
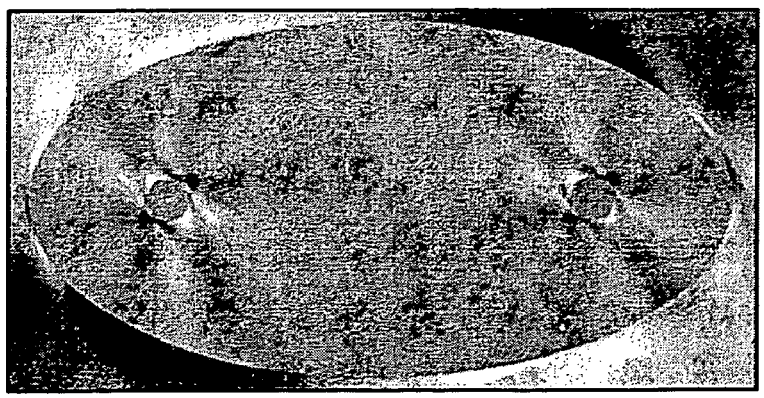
FIG. 15 A representation of a differentiation image of the images shown in FIGS. 13 and 14.

FIG. 15 then shows the differential image of the cross-section images from FIGS. 13 and 14. The errors reach approximately +/−20 HU in the soft tissue.

The method described here and the x-ray system 1 described here has a number of advantages.

With the x-ray system 1, the dose of the x-ray radiation can be minimized. By correcting the voltage dependent multispectral radiation hardening, the image quality is improved at the same time. This substantially increases the quantitative accuracy of the reconstructed volumetric images. Hardening artifacts are largely eliminated.

This means that it is then possible to consider the use of the method described here also in conjunction with conventional computer tomography devices that have a fixed frame in which the x-ray source and the x-ray detector rotate.

It is pointed out that the method described here can be realized using software or with the aid of hardware. It is also pointed out that the term evaluation unit is to be understood as being functional. The evaluation unit does not necessarily have to be formed by a physical unit but instead the function of an evaluation unit can also be performed by several physical units.

It should finally be pointed out that with the exemplary embodiment described here the tube voltage of the x-ray tube has been used to vary the energy distribution of the x-ray radiation. It is also conceivable to vary other operating parameters of the x-ray system 1. For example, the energy distribution of the x-ray radiation can also be varied by using filters. In this case, the multiparameter correction table C must also be calculated relative to the additional operating parameters. Other operating parameters that influence the energy distribution of the x-ray radiation can be taken into account for other x-ray sources that are used instead of the x-ray tube.

The invention claimed is:

1. A computer tomography medical examination device, comprising:
    a radiation source for x-raying an object being medically examined from a projection direction with a radiation energy associated to the projection direction;
    a detector for detecting a radiation from the radiation source and recording a projection image of the object;
    a data memory for storing a predetermined correction value; and
    an evaluation unit connected downstream of the detector for correcting a radiation hardening of the projection image,
    wherein an operating parameter of the radiation source is applied to determine the radiation energy associated to the projection direction which depends on an absorption characteristics of the object,
    wherein the evaluation unit is provided with the operating parameter and reads the predetermined correction value allocated to the operating parameter and corrects a radiation hardening on the projection image.

2. The device as claimed in claim 1, wherein the radiation source is an x-ray tube and the detector is an x-ray detector.

3. The device as claimed in claim 1, wherein a variable of the operating parameter is an x-ray tube voltage.

4. The device as claimed in claim 1, wherein the evaluation unit reads the predetermined correction value relative to the x-ray tube voltage from the data memory and carries out a water correction on the projection image by the predetermined correction value.

5. The device as claimed in claim 1, wherein the evaluation unit performs a post-reconstructive correction of an hardening on the projection image that is caused by an attenuation which is different than a water-equivalent material in the object.

6. The device as claimed in claim 5, wherein the post-reconstructive correction of the hardening of the projection image is carried out iteratively by the evaluation unit.

7. The device as claimed in claim 5, wherein the post-reconstructive correction of the hardening of the projection image is carried out by the evaluation unit with a spatial resolution that is less than a spatial resolution of the projection image.

8. The device as claimed in claim 1,
wherein an object model differentiated according to the absorption characteristics of the object is determined by the evaluation unit from the projection image,
wherein an object data record derived from the object model is allocated by the evaluation unit to a pixel of the projection image,
wherein the correction value for the projection image is determined by the evaluation unit using the object data record and the x-ray tube voltage.

9. The device as claimed in claim 1, wherein the object is a live animal or human patient.

10. A method for correcting a radiation hardening on a projection image of an object being medically examined, comprising:
x-raying the object by a radiation source from a projection direction with a radiation energy associated to the projection direction;
detecting a radiation from the radiation source and recording a projection image of the object by a detector;
storing a predetermined correction value in a data memory;
correcting the radiation hardening of the projection image by an evaluation unit connected downstream of the detector; and
providing a corrected projection image,
wherein an operating parameter of the radiation source is applied to determine the radiation energy associated to the projection direction which depends on an absorption characteristics of the object,
wherein the evaluation unit is provided with the operating parameter and reads the predetermined correction value allocated to the operating parameter and corrects a radiation hardening on the projection image.

11. The method as claimed in claim 10, wherein the radiation source is an x-ray tube and the detector is an x-ray detector and the projection image is generated by the x-ray tube and the x-ray detector.

12. The method as claimed in claim 10, wherein the tube voltage is used as a variable of the operating parameter.

13. The method as claimed in claim 10, wherein a water correction on the projection image is carried out by the evaluation unit by reading a predetermined correction value from the data memory relative to the tube voltage applied.

14. The method as claimed in claim 10, wherein a post-reconstructive correction of the radiation hardening on the projection image is performed by the evaluation unit relative to the tube voltage, the hardening caused by a material having a different attenuating effect than a water-equivalent material.

15. The method as claimed in claim 14, wherein the post-reconstructive correction of the hardening is performed iteratively by the evaluation unit.

16. The method as claimed in claim 14, wherein the post-reconstructive correction of the hardening is performed with a spatial resolution that is less than a spatial resolution of the project image data.

17. The method as claimed in claim 10,
wherein a three-dimensional object model differentiated according to an absorption characteristics of the object is determined by the evaluation unit from the projection image,
wherein an object data record is derived from the object model and is allocated to the project image,
wherein the object data record and the tube voltage are used to determine a correction value for the projection image from the data memory.

18. The method as claimed in claim 10, wherein the object is a live animal or human patient.

* * * * *